United States Patent [19]

Métivier et al.

[11] Patent Number: 5,414,148
[45] Date of Patent: May 9, 1995

[54] PREPARATION OF P-NITROPHENOLIC COMPOUNDS

[75] Inventors: Pascal Métivier, Lyons; Laurent Bernard, Venissieux, both of France

[73] Assignee: Rhone-Poulenc Chimie, Courbevoie Cedex, France

[21] Appl. No.: 249,200

[22] Filed: May 26, 1994

[30] Foreign Application Priority Data

May 26, 1993 [FR] France ................. 93 06325

[51] Int. Cl.$^6$ ............... C07C 205/20; C07C 205/21; C07C 205/26
[52] U.S. Cl. ................... 568/706; 568/650; 568/705; 568/709
[58] Field of Search ........... 568/706, 650, 705, 709, 568/652

[56] References Cited

U.S. PATENT DOCUMENTS

| | | | |
|---|---|---|---|
| 1,502,849 | 7/1924 | Ehrlich | 568/706 |
| 3,320,324 | 5/1967 | Kouba | 568/706 |
| 3,510,527 | 5/1970 | Prosser | 568/706 |
| 3,517,075 | 6/1970 | Callister | 568/706 |

FOREIGN PATENT DOCUMENTS

| | | |
|---|---|---|
| 1493827 | 6/1969 | Germany . |
| 1965384 | 7/1970 | Germany . |
| 1165637 | 10/1969 | United Kingdom . |

*Primary Examiner*—Werren B. Lone
*Attorney, Agent, or Firm*—Burns, Doane, Swecker & Mathis

[57] ABSTRACT p-Nitrophenolic compounds, e.g., p-nitrophenol itself, are selectively prepared by (a) reacting a phenolic compound with a nitrosating agent in the presence of sulfuric acid, the concentration of which $H_2SO_4$ being at least 60%, (b) oxidizing the p-nitrosophenolic compound thus formed with nitric acid, the concentration of sulfuric acid in the medium of reaction, upon completion of oxidation, being no greater than 80%, and (c) separating the p-nitrophenolic compound which thus precipitates.

24 Claims, No Drawings

PREPARATION OF P-NITROPHENOLIC COMPOUNDS

BACKGROUND OF THE INVENTION

1. Field of the Invention

The present invention relates to the preparation of nitrophenolic compounds, and, more especially, to the selective preparation of p-nitrophenol.

2. Description of the Prior Art

Various processes are known to this art for the preparation of p-nitrophenol.

In particular, U.S. Patent No. 3,517,075 describes a process for the preparation of p-nitrophenol via oxidation of p-nitrosophenol. In a first stage, the p-nitrosophenol is prepared by the nitrosation of phenol using nitrous acid, in the presence of sulfuric acid. Then, in a second stage, the p-nitrosophenol is oxidized into p-nitrophenol.

A major disadvantage of such a process is that p-nitrosophenol precipitates. This being an unstable compound, significant risks of thermal explosion are presented.

SUMMARY OF THE INVENTION

Accordingly, a major object of the present invention is the provision of an improved process for the preparation of p-nitrophenolic compounds, in particular p-nitrophenol, that avoids the aforesaid safety disadvantage to date plaguing this art.

Briefly, the present invention features a process for the preparation of p-nitrophenolic compounds by the nitrosation of phenolic substrates in the presence of sulfuric acid, followed by oxidation of the p-nitrosophenolic compound thus formed by means of nitric acid, wherein said first nitrosation stage, the sulfuric acid concentration is at least equal to 60%. In the second stage, upon completion of the oxidation reaction, the sulfuric acid concentration is at the most equal to 80%. This effects precipitation of the p-nitrophenolic compound, which is then separated.

DETAILED DESCRIPTION OF BEST MODE AND PREFERRED EMBODIMENTS OF THE INVENTION

More particularly according to the present invention, by controlling the sulfuric acid concentration in the two nitrosation and oxidation stages, the problem of the explosiveness of, for example, p-nitrosophenol, is avoided. This is because, by selecting a sulfuric acid concentration above 60% in the first stage, the p-nitrosophenol is then soluble. On the other hand, the precipitated p-nitrophenol is recovered at the end of the oxidation stage, wherein the sulfuric acid concentration is below 80%, as said p-nitrophenol is soluble at higher concentrations thereof.

Thus, it has now surprisingly been found that p-nitrosophenol is soluble under the conditions of the process of the invention.

The process according to the present invention is not only applicable to phenol, per se, but also to any aromatic compound substituted by an —OH functional group, presupposing that the position para to the hydroxyl group bears no substituent.

The preferred hydroxylated compound starting materials of this invention have the general formula:

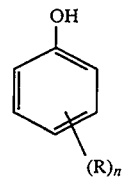

in which R is a hydrogen atom, an alkyl or alkoxy radical having from 1 to 4 carbon atoms, preferably a methyl or ethyl radical, a perfluoroalkyl radical having from 1 to 4 carbon atoms, or a halogen atom, preferably chlorine, bromine or fluorine, and n is a number equal to 0, 1 or 2.

Thus, the present invention does not exclude the existence of other substituents on the aromatic ring member, to the extent that any such substituent(s) do not interfere with any of the steps of reaction of the subject process. In particular, various functional groups or halogen atoms may be present on the alkyl substituents borne by the aromatic nucleus, and such alkyl, etc., moieties may be interrupted by one or more heteroatoms, e.g., oxygen, nitrogen or sulfur.

Thus, by the term "phenolic compound" according to this invention, are intended phenol, per se, as well as any hydroxylated aromatic compound as indicated above, particularly having the aforesaid general structural formula.

According to the process of the invention, the phenol is subjected to nitrosation in the first stage, in the presence of sulfuric acid.

As indicated above, the amount of sulfuric acid employed is particularly critical. The sulfuric acid concentration in the reaction medium, expressed by the weight ratio of sulfuric acid to sulfuric acid+water, is at least equal to 60% by weight. Advantageously, the sulfuric acid concentration ranges from 60% to 90% and preferably from 70% to 80% by weight.

The presence of water in the nitrosation stage is not problematical, to the extent that the amount thereof is such that the aforesaid sulfuric acid concentration is observed.

The nitrosation agent can be any $NO^+$ source. Thus, it is possible to use nitrogen dioxide $NO_2$, nitrogen trioxide $N_2O_3$, nitrogen peroxide (tetraoxide) $N_2O_4$, nitrogen oxide $NO$ associated with an oxidizing agent such as, e.g., nitric acid, nitrogen dioxide or oxygen. In the event that the nitrosation agent is gaseous under the reaction conditions, it is bubbled into the reaction medium.

It is also possible to use nitrous acid, a nitrose or nitrosyl sulfate, or a nitrous salt, preferably an alkali metal salt and, even more preferably, sodium.

The amount of nitrosation agent can vary widely. When it is expressed by the molar ratio of phenol to nitrosation agent defined as $NO^+$, it is at least equal to the stoichiometric amount, but it is preferable to employ a stoichiometric excess of up to 500%, preferably a stoichiometric excess of from 150% to 300%.

As regards the concentration of the phenolic substrate in the reaction medium, same preferably ranges from 2% to 20% by weight.

The phenol is typically introduced in liquid form. Thus, it can either be introduced in the molten state, or mixed with water. In the latter case, mixtures containing 60% to 90% phenol are suitable. It must be ensured that the water content in the reaction medium is such that the above sulfuric acid concentration is respected.

In the following stage, the p-nitrosophenol is oxidized by means of nitric acid. It is also possible to employ a precursor of nitric acid, e.g., nitrogen peroxide.

An aqueous nitric acid solution is advantageously used, having a concentration which can range from 30% to 100%, but a concentration of from 60% to 100% is preferred.

The amount of nitric acid, expressed by the molar ratio of phenol to nitric acid, generally ranges from 0.9 to 1.2 and preferably from 0.95 to 1.05.

As indicated above, the amount of sulfuric acid must be especially controlled in this stage.

The sulfuric acid concentration is thus equal to or less than 80%. The lower limit is not critical. It advantageously ranges from 50% to 80% and preferably from 65% to 75%.

During the nitrosation reaction, water can form. During the oxidation reaction, it may be necessary to add water in order to provide the aforesaid sulfuric acid concentrations. Generally, the water is added at the same time as the nitric acid.

The process according to the invention is advantageously carried out at a temperature of from 0° to 40° C. and preferably from 10° to 30° C.

The process of the invention is generally carried out under atmospheric pressure, but can also be conducted under slightly reduced pressure, e.g., from 500 to 760 mm of mercury (66500 and 101080 Pa), or under pressure, e.g., of up to 5 bars.

In a preferred embodiment of the invention, the nitrosation stage is carried out under a controlled inert gas atmosphere. It is possible to establish an atmosphere of rare gases, preferably argon, but it is more economic to use nitrogen.

From a practical standpoint, the process according to the invention is easy to carry out, because it does not require the use of specific apparatus. In actual practice, the process of the invention is readily carried out as follows.

The different constituents of the reaction mixture are charged into the selected apparatus/reactor. This can be accomplished via any one of a number of different techniques. A first embodiment entails first charging the sulfuric acid solution and then adding, in parallel, the phenol and the nitrosation agent. In another embodiments, the sulfuric acid solution and the nitrosation agent are introduced, followed by the addition of phenol, preferably in portions, or continuously by pouring. Another embodiment is based on the parallel introduction to a sediment of a phenol, on the one hand, and the sulfuric acid and nitrosation agent on the other.

Following introduction of the reagents, the reaction mixture is maintained in the aforementioned temperature range; it may be appropriate to cool the reaction mixture.

In the downstream oxidation stage, the nitric acid is introduced into the reaction medium containing the p-nitrosophenol. It can be added all at once, or progressively, in portions or in continuous manner by pouring. It is also possible to introduce the nitric acid at the beginning, e.g., in parallel with the addition of phenol. The temperature of the reaction mixture is maintained within the above range.

In another embodiment of the invention, the nitric acid is formed in situ from the nitrogen peroxide, which serves both as a nitrosation agent in the first stage and a nitric acid precursor in the second stage. To this end, the nitrogen peroxide is introduced at the outset and, in the second stage, is heated to a temperature of from 20° to 40° C. As a consequence of the concentration of sulfuric acid in the reaction mixture, the p-nitrophenol precipitates.

The precipitate obtained is separated according to conventional solid/liquid separation techniques, preferably by filtration. The precipitate obtained is washed, preferably by a sulfuric acid solution having the same concentration as that in the oxidation stage. To remove impurities from the precipitate, it can be washed with water.

The mother liquors collected after each separation can be recycled. They are rich in nitrosation agent, because the latter is regenerated during oxidation.

The process according to the invention permits the essentially selective preparation of p-nitrophenol, because the amount of o-nitrophenol produced is typically less than 5%.

Moreover, according to the invention the p-nitrophenol precipitates preferentially as compared with the o-nitrophenol and the dinitrophenols obtained as impurities.

The p-nitrophenolic final products according to this invention, notably p-nitrophenol, are useful intermediates for the preparation of, e.g., N-acetyl-p-aminophenol, via the reduction of p-nitrophenol and acetylation of the p-aminophenol thus produced.

For a description of such techniques, see, for example, Kirk-Othmer, *Encyclopedia of Chemical Technology*, volume 2, Third Edition. The reduction of p-nitrophenol is carried out in conventional manner, e.g., by contacting same with hydrogen in the presence of a hydrogenation catalyst, preferably a precious metal, for example platinum or palladium. Such catalyst can be deposited onto suitable support, whether charcoal, acetylene black, silica, alumina, or the like.

The aforenoted acetylation is preferably carried out using acetic anhydride.

In order to further illustrate the present invention and the advantages thereof, the following specific examples are given, it being understood that same are intended only as illustrative and in nowise limitative.

In said examples to follow:

$$TT = \frac{\text{number of moles of phenol converted}}{\text{number of moles of phenol introduced}}\ \%$$

$$RT = \frac{\text{number of moles of nitrophenol formed}}{\text{number of moles of phenol converted}}\ \%$$

EXAMPLE 1

Into a 1 liter reactor provided with a double envelope, a mechanical stirring system and a temperature probe were charged 500 ml of an aqueous 80% by weight sulfuric acid solution and 97.4 g of an aqueous 42.5% $NaNO_2$ solution (i.e., 0.6 mole of $NaNO_2$) were added thereto.

The reaction mixture was cooled to 10° C. and, over 40 min, while maintaining the temperature at 10° C., 33.7 g of an aqueous 80% phenol solution (i.e., 0.286 mole of phenol) were poured therein.

The reaction mixture was then maintained for 5 min at 10° C. and then, over 10 min, 30.1 g of an aqueous 67% by weight nitric acid solution were added (0.32 mole), also while maintaining the temperature at 10° C. The reaction mixture became heterogeneous.

The reaction mixture was maintained at 10° C. and then filtered. The filter cake was washed twice, each time with 50 g of an aqueous 70% sulfuric acid solution, then water, followed by drying in vacuo by means of the water jet pump. Thus, 32.94 g of a light grey product titrating 95.2% p-nitrophenol were recovered.

The filtrate and the wash waters were recovered and analyzed by high performance liquid chromatography.

The results obtained for the reaction were as follows:
$TT_{phenol} = 100\%$
$RT_{p-nitrophenol} = 92\%$
$RT_{o-nitrophenol} = 0.6\%$
$RT_{dinitrophenols} = 0.93\%$

EXAMPLE 2

Into a 250 ml reactor equipped with a mechanical stirring system and a temperature regulating system were charged 100 ml (173 g) of an aqueous 80% sulfuric acid solution. Next, 13 ml (15.3 g) of an aqueous 27% sodium nitrite solution (0.06 mole of $NaNO_2$) were added thereto. The reaction medium was adjusted to 10° C.

Then, over 40 min, 6.7 ml of an aqueous 80% phenol solution were introduced (0.0605 mole of phenol), while maintaining the temperature at 10° C. After 2 minutes of phenol addition, over 38 min 6.9 ml of an aqueous 40% nitric acid solution (0.550 mole of nitric acid) were simultaneously introduced.

The reaction medium became heterogeneous. The reaction medium was maintained for 5 min at 10° C. and filtered cold. The filter cake was washed twice with 30 ml of an aqueous 70% sulfuric acid solution and then three times with water (30 ml), followed by drying in vacuo.

This provided 5.54 g of a solid product titrating 95% in p-nitrophenol. The filtrates and wash waters were combined and analyzed.

The results obtained for the reaction were as follows:
$TT_{phenol} = 100\%$
$RT_{p-nitrophenol} = 6.7\%$
$RT_{o-nitrophenol} = 6.7\%$
$RT_{dinitrophenols} = 0.7\%$
$RT_{p-nitrosophenol} = 6.8\%$

EXAMPLE 3

The procedure of Example 2 was repeated exactly, except that the temperature was maintained at 26° C. throughout the test.

The following results were obtained:
$TT_{phenol} = 100\%$
$RT_{p-nitrophenol} = 62.5\%$
$RT_{o-nitrophenol} = 5.4\%$
$RT_{dinitrophenols} = 1.3\%$
$RT_{p-nitrosophenol} = 12.0\%$

EXAMPLE 4

Into a 250 ml reactor equipped with a double envelope and a mechanical stirring system were charged 100 ml of an aqueous 80% sulfuric acid solution, followed by the addition of 19.5 g of aqueous 42.5% sodium nitrite solution (0.12 mole of $NaNO_2$).

Then, over 40 min, 7.07 g of an aqueous 80% phenol solution were introduced (0.0602 mole), while maintaining the temperature at 25° C. The reaction mixture was then maintained at 25° C. for 5 min, and, over 15 min, 5.44 g of aqueous 67% nitric acid solution (0,058 mole) were added.

The mixture was maintained at 25° C. for 5 min. The medium was heterogeneous solid/liquid. HPLC analysis of the different species provided the following results:
$TT_{phenol} = 100\%$
$RT_{p-nitrophenol} = 89.5\%$
$RT_{o-nitrophenol} = 0.75\%$
$RT_{dinitrophenols} = 2.05\%$

EXAMPLE 5

The procedure of Example 4 was repeated, except that the temperature was 10° C. The introduction of the nitric acid was in two batches. 0.7 g of nitric acid (0.0074 mole) were added to the medium of sulfuric acid and sodium nitrate prior to addition of the phenol, and 5.6 g of nitric acid (0.0595 mole) were introduced after the phenol had been poured.

The final reaction medium was heterogeneous. It was filtered and the phases analyzed. The following results were obtained:
$TT_{Phenol} = 100\%$
$RT_{p-nitrophenol} = 91.1\%$
$RT_{o-nitrophenol} = 1.5\%$
$RT_{dinitrophenols} = 0.8\%$

EXAMPLE 6

Into a 1 liter reactor equipped with a double envelope and a mechanical stirring system were introduced 904 g of an aqueous 70% sulfuric acid solution and 18.5 g of a 68% nitric acid solution (0.2 mole $HNO_3$). 13 g of gaseous nitrogen oxide NO (0.43 mole) were introduced into the liquid mixture, accompanied by stirring.

The temperature of this reaction mixture was adjusted to 10° C., followed by the addition of 35.2 g of an aqueous 80% phenol solution, over 40 min, while maintaining the temperature at 10° C. Then, the reaction medium was maintained at 10° C. for 5 min and 28.2 g (0.3 mole) of aqueous 68% nitric acid solution were introduced over 15 min into the reaction medium. The reaction medium was maintained at the temperature of 10° C. for 5 min. The reaction medium was then filtered.

This provided 15.8 g of a dark red solid. This solid and the remaining mother liquors were analyzed by high performance liquid chromatography. The following reaction results were obtained:
$TT_{phenol} = 100\%$
$RT_{p-nitrophenol} = 61\%$
$RT_{o-nitrophenol} = 4.6\%$
$RT_{dinitrophenols} = 8.8\%$

EXAMPLE 7

Into a double-envelope reactor equipped with a mechanical stirring system were charged 440.5 g of an aqueous 69% sulfuric acid solution and 40.5 g of nitrosyl acid sulfate $NO_2OSO_3H$ (0.3 mole). The reaction mixture was cooled to 10° C. and 17.7 g of an aqueous 80% phenol solution (0.15 mole) were poured into the reaction mixture, over 40 min, while maintaining the temperature at 10° C.

The reaction mixture was then maintained at 10° C. for 5 min, and 13.9 g of an aqueous 68% nitric acid solution (0.15 mole) were added to the reaction mixture, over 15 min, while maintaining the temperature at 10° C.

The reaction mixture was then filtered. The filter cake was washed twice with 30 ml of an aqueous 70% sulfuric acid solution and then three times with 30 ml of water, followed by the drying of the product in vacuo. 18 g of a light yellow precipitate were obtained, essentially consisting of p-nitrophenol.

Analysis of the different phases provided the following results:

TT$_{phenol}$=100%
RT$_{p-nitrophenol}$=88%
RT$_{o-nitrophenol}$=1.1%
RT$_{dinitrophenols}$=1.75%

EXAMPLE 8

Into a double envelope reactor equipped with a mechanical stirring system were charged 440 g of an aqueous 70% sulfuric acid solution and 40.5 g of nitrosyl acid sulfate (0.3 mole). 17.7 g of an aqueous 80% phenol solution (0.15 mole) were introduced over 10 minutes, while maintaining the temperature at 25° C. The reaction mixture was then maintained at 25° C. for 5 min, followed by the addition thereto of 14.5 g of an aqueous 68% nitric acid solution (0.156 mole), over 15 min, while maintaining the temperature at 25° C. The reaction mixture was maintained at 25° C. for 5 min and then filtered.

The filter cake was washed twice with 30 ml of an aqueous 70% sulfuric acid solution and then thrice with 30 ml of water. This provided 12.1 g of a grey solid titrating 98% in p-nitrophenol.

The different phases were analyzed by high performance liquid chromatography and the following results were obtained:

TT$_{phenol}$=100%
RT$_{p-nitrophenol}$=90%
RT$_{o-nitrophenol}$=0.2%
RT$_{dinitrophenols}$=3.38%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims., including equivalents thereof.

What is claimed is:

1. A process for the preparation of a p-nitrophenolic compound, comprising (a) reacting a phenolic compound with a nitrosating agent in the presence of sulfuric acid, the concentration of which H$_2$SO$_4$ being at least 60%, (b) oxidizing the p-nitrosophenolic compound thus formed with nitric acid, the concentration of sulfuric acid in the medium of reaction, upon completion of oxidation, being no greater than 80%, and (c) separating the p-nitrophenolic compound which thus precipitates.

2. The process as defined by claim 1, the concentration of sulfuric acid in the nitrosation step (a) ranging from 60% to 90%.

3. The process as defined by claim 2, the concentration of sulfuric acid in the nitrosation step (a) ranging from 70% to 80%.

4. The process as defined by claim 1, said nitrosating agent comprising a source of NO$^+$.

5. The process as defined by claim 4, said NO$^+$ source comprising nitric oxide (NO) and an oxidizing agent, nitrogen dioxide (NO$_2$), nitrogen trioxide (N$_2$O$_3$), nitrogen tetraoxide (N$_2$O$_4$), nitrous acid, nitrosyl sulfate, or a nitrous salt.

6. The process as defined by claim 5, said NO$^+$ source comprising an alkali metal nitrous salt.

7. The process as defined by claim 1, wherein the amount of nitrosating agent employed in said step (a) is at least the stoichiometric amount.

8. The process as defined by claim 7, the step (a) being carried out employing up to a 500% stoichiometric excess of said nitrosating agent.

9. The process as defined by claim 1, the concentration of the phenolic substrate in the step (a) reaction medium ranging from 2% to 20% by weight.

10. The process as defined by claim 1, the concentration of sulfuric acid in the oxidation step (b) ranging from 50% to 80%.

11. The process as defined by claim 10, the concentration of sulfuric acid in the oxidation step (b) ranging from 65% to 75%.

12. The process as defined by claim 1, comprising (b) oxidizing the p-nitrosophenolic compound thus formed with an aqueous nitric acid solution, or a nitric acid precursor.

13. The process as defined by claim 12, comprising (b) oxidizing the p-nitrosophenolic compound with an aqueous nitric acid solution, the concentration of which ranging from 30% to 100% by weight.

14. The process as defined by claim 13, said concentration ranging from 60% to 100% by weight.

15. The process as defined by claim 1, wherein the amount of nitric acid, expressed by the molar ratio of phenolic compound to nitric acid, ranges from 0.9 to 1.2.

16. The process as defined by claim 15, said molar ratio ranging from 0.95 to 1.05.

17. The process as defined by claim 1, carried out at a temperature ranging from 0° to 40° C.

18. The process as defined by claim 17, carried out at a temperature ranging from 10° to 30° C.

19. The process as defined by claim 1, wherein step (a) the phenolic compound and nitrosating agent are introduced into said sulfuric acid, or the phenolic compound is introduced into said sulfuric acid and nitrosating agent, or said reagents are conjointly introduced.

20. The process as defined by claim 1, wherein step (b) the nitric acid is introduced, whether all at once or progressively, into the medium of reaction comprising said p-nitrosophenolic compound.

21. The process as defined by claim 1, comprising conjointly introducing said nitric acid and said phenolic compound into the medium of reaction.

22. The process as defined by claim 12, comprising (b) oxidizing the p-nitrosophenolic compound with nitric acid formed in situ from nitrogen tetraoxide.

23. The process as defined by claim 1, said phenolic compound being phenol.

24. The process as defined by claim 1, said phenolic compound having the formula:

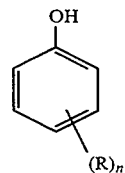

in which R is an alkyl or alkoxy radical having from 1 to 4 carbon atoms, a perfluoroalkyl radical having from 1 to 4 carbon atoms, or a halogen atom, and n is 1 or 2, with the proviso that no substituent R occupies the position para to the hydroxyl group.

* * * * *